United States Patent [19]

Johnson et al.

[11] Patent Number: 4,493,206
[45] Date of Patent: Jan. 15, 1985

[54] EROSION TEST APPARATUS

[75] Inventors: Richard C. Johnson; Allyn P. Norris, both of Dansville, N.Y.

[73] Assignee: Foster Wheeler Energy Corporation, Livingston, N.J.

[21] Appl. No.: 378,537

[22] Filed: May 17, 1982

[51] Int. Cl.³ .............................................. G01N 3/56
[52] U.S. Cl. .......................................... 73/7; 384/317
[58] Field of Search ...................... 73/7; 384/313, 315, 384/317

[56] References Cited

U.S. PATENT DOCUMENTS

| | | | |
|---|---|---|---|
| 1,476,775 | 12/1923 | Sproull | 73/7 |
| 1,961,333 | 6/1934 | Burns | 73/7 |
| 2,008,527 | 7/1953 | Warren | 384/315 |
| 3,653,252 | 4/1972 | Neff et al. | 73/7 |

FOREIGN PATENT DOCUMENTS

| | | | |
|---|---|---|---|
| 23555 | 10/1882 | Fed. Rep. of Germany | 384/313 |
| 2632977 | 1/1978 | Fed. Rep. of Germany | 384/317 |
| 200267 | 7/1967 | U.S.S.R. | 73/7 |
| 502294 | 4/1976 | U.S.S.R. | 73/7 |
| 715969 | 2/1980 | U.S.S.R. | 73/9 |
| 763741 | 9/1980 | U.S.S.R. | 73/7 |

OTHER PUBLICATIONS

Doroshuk, Machine for Friction and Wear Tests on Materials over a Wide Range of Atmospheric Conditions, Feb. 1970.
Drobinin, Method of Investigating the Wear of Hard Tungsten Carbide Alloys in Liquid Nitrogen, Feb. 1972.
Tuznikov et al., Setup to Determining the High Temperature Antifriction Characteristics of Material Subjected to Friction, Sep. 1974.

*Primary Examiner*—Gerald Goldberg
*Assistant Examiner*—Hezron E. Williams
*Attorney, Agent, or Firm*—Marvin A. Naigur; John E. Wilson; Thomas L. Adams

[57] ABSTRACT

A test apparatus can test the erosion resistance of a specimen. The apparatus has an enclosure containing in its test chamber an abrasive medium. Also included is a spindle attached to the enclosure. The spindle has an inside end adapted to hold the specimen. A motor coupled to the spindle can spin the inside end at an adjustable angular speed within the medium. Preferably, a thermal jacket can moderate temperature within the spindle apparatus. The apparatus is used to spin the specimen through the abrasive medium at a chosen speed and then measure the extent of erosion.

35 Claims, 5 Drawing Figures

EROSION TEST APPARATUS

BACKGROUND OF THE INVENTION

The present invention relates to test apparatus for determining erosion and, in particular, to apparatus for spinning a specimen in an abrasive medium.

To facilitate preventative maintenance, it is useful to estimate in advance the annual wear that can be expected within a vessel, pipe or other device. For example, a vessel or pipe fabricated from a special alloy and/or lined with a ceramic coating or other castable refractory material may be subjected to a service environment wherein high speed particles impinge against the interior of the pipe or vessel at glancing angles. Furthermore, these particles may be at a fairly high (or low) temperature and be propelled by a corrosive gaseous ambient. The particles can constitute any material or mixture of materials including coal, catalyst, sand, shale, sulphur silicon carbide, or other abrasive material. These particles can typically range in size between 10 to 1000 μm at speeds between 0.01 to 400 feet per second, although other speeds and sizes are possible.

A known erosion resistance test is disclosed in ASTM 704-76A, entitled "Standard Method for Abrasion Resistance of Refractory Material at Room Temperature." In the test, size graded silicon carbide is blasted by air pressure normally against a flat specimen. The extent of erosion over a predetermined interval is used as a measure of the erosion resistance of the specimen. However, this high angle of incidence at a high velocity is often unrepresentative of the conditions under whih a specimen is actually used. Such a test takes into account neither the actual, small, glancing angles of the particles nor the actual temperatures, nor the effect of a corrosive gaseous ambient. Furthermore, an unrepresentatively high-velocity, normal collision by a particle may cause unrepresentative microfracture of a brittle non-metallic target such as glass, refractories, bricks etc.

In a known test method (for example, expired U.S. Pat. No. 1,961,333) a disc is rotated in a hopper containing sand or finely divided carborundum. This disc is rotated for a predetermined length of time while the revolutions are counted, in order to measure the wearing qualities of a surface finish. However, this apparatus is not useful for simulating a specific environment. Furthermore, this known apparatus does not employ a variable speed motor for rotating a disc at a speed which simulates the speed of particles impinging on the disc under a specific service environment. Also, this known apparatus is not useful for testing the disc with a hot abrasive medium since its hopper is neither insulated nor are the bearings protected against high temperatures.

Accordingly, there is a need for a rapid, simple, and effective erosion test that simulates the erosion occurring under actual service conditions.

SUMMARY OF THE INVENTION

In accordance with the illustrative embodiments demonstrating features and advantages of the present invention, there is provided test apparatus for testing the erosion resistance of a specimen. The apparatus includes an abrasive medium disposed in the test chamber of an enclosure. A spindle means is attached to the enclosure and has an inside end adapted to hold the specimen. Also included is a motor means coupled to the spindle means for spinning its inside end at an adjustable angular speed within the medium.

Also, in accordance with the same invention, the foregoing spindle means is used to hold the above specimen in the foregoing test chamber of the enclosure within the abrasive medium. A thermal means is also included for moderating temperature within the spindle means.

Also in accordance with the present invention, a method is provided for testing the erosion properties of a specimen exposed to glancing impingement by particles having a given speed. The method includes the step of embedding the specimen in a multiplicity of the particles. The specimen is spun at an angular velocity bearing a given relation to the given speed. The method also includes a step of measuring the extent of erosion from the specimen.

By employing such apparatus and method, erosion testing can be performed under conditions simulating the actual service environment. In a preferred embodiment, the specimen is in the shape of a disc that is attached to a spindle supported by a high temperature bearing. This bearing is mounted within a fluid cooled jacket or tank. Therefore, the bearings can operate at a relatively high angular speed even though the test may be conducted with materials at a high temperature. Also this preferred embodiment employs an enclosure that is in the form of a drum having insulated walls. To simulate a hot abrasive medium, the enclosure can be filled partially or completely with particles preheated to a relatively high temperature simulating that existing under service conditions. The disc is then rotated at a speed that produces a tangential velocity equivalent to the speed of particles existing in the service environment. Thereafter, the erosion of the specimen is measured either by measuring weight reduction or the reduction in diameter.

It has been found that this method and apparatus can be employed to produce a rate of erosion that stabilizes very rapidly after initiation of the test to a constant linear rate. If the amount of erosion is plotted, it can be projected to an annual wear rate.

BRIEF DESCRIPTION OF THE DRAWINGS

The above brief description as well as other objects, features and advantages of the present invention will be more fully appreciated by reference to the following detailed description of the presently preferred but nonetheless illustrative embodiment in accordance with the present invention when taken in conjunction with the accompanying drawings wherein.

DETAILED DESCRIPTION OF THE PREFERRED EMBODIMENT

Figure 1:
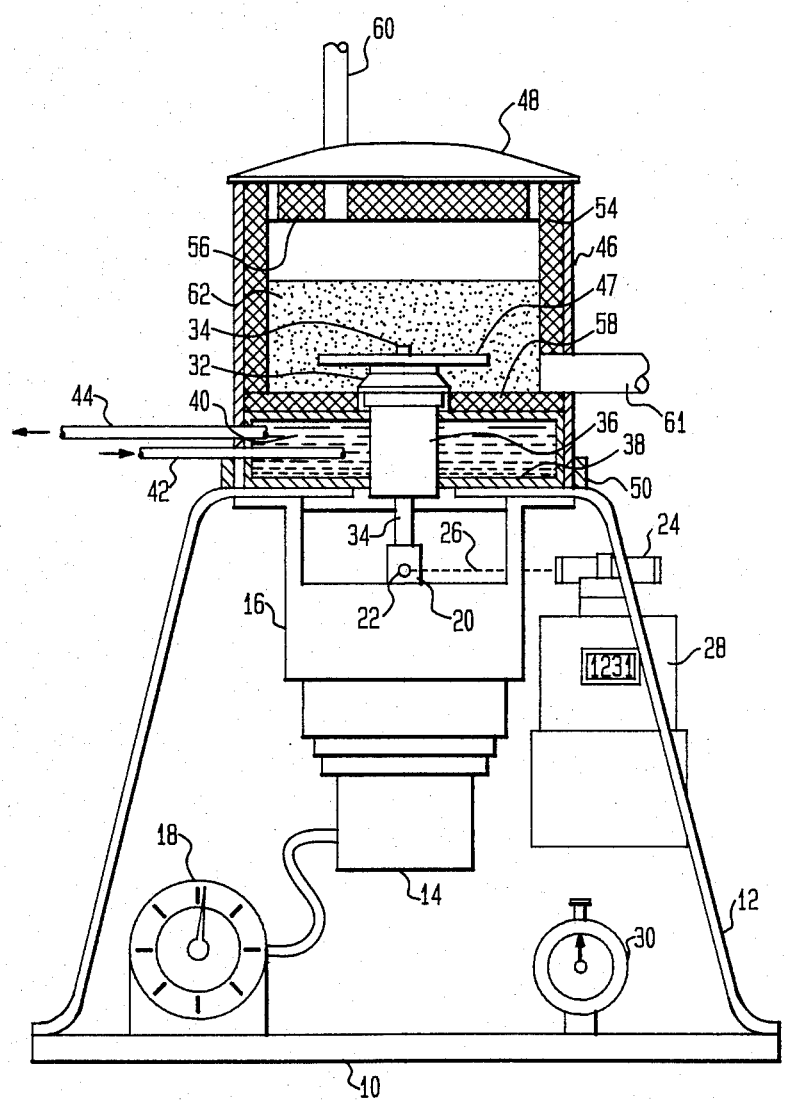
FIG. 1 is an elevational view, partly in section, of test apparatus according to the principles of the present invention.

Referring to FIG. 1, a test apparatus is shown supported on legs 12 resting on platform 10. A motor means, shown herein as a DC motor 14, can operate at a variable speed from zero to in excess of 25,000 revolutions per minute. It will be appreciated, of course, that different types of driving devices operable at different speeds are possible and may employ AC (alternating current) motors, pneumatic motors, etc. Motor 14 is mounted in an adjusting bracket 16 which is attached below the upper portions of legs 12 and which allows motor 14 to be axially adjusted. Bracket 16 is in the form of a flanged collar which can grip motor 14 at any one of various positions to enable the axial positioning of motor 14. Motor 14 is provided with a means for adjusting motor speed, in this embodiment a manually adjustable rheostat 18 is used to set the DC (direct current) voltage applied to motor 14. Motor 14 has an output coupling 20 in the form of a chuck having on its periphery a reflective target 22.

This reflective target 22 is part of an optical transceiving means including an optical transceiver 24 which can emit light along path 26 and receive a reflection from reflective target 22 along the same path. Thus, transceiver 24 can detect the revolutions of motor 14. Transceiver 24 drives a counter 28 to accumulate the total number of elapsed revolutions of motor 14. Also included and mounted on base 10 is a stop watch 30. It will be appreciated that counter 28 together with timer 30, can be employed as a means for measuring the angular speed of motor 14. Alternatively, the counter 28 can employ an internal timing mechanism so that the elapsing revolutions measured by transceiver 24 can be used to display directly an angular speed. Alternatively, a tachometer or other device can be used to measure angular speed.

A spindle means, shown herein as hub 32, connects to coaxial shaft 34 running through bearing 36. Shaft 34 and hub 32 rotate together. The lower end of shaft 34 is connected to motor 14 by chuck 20. Encircling bearing 36 is a thermal means, shown herein as a heat exchanging jacket 38. Jacket 38 is in the shape of a hollow cylindrical tank having top and bottom concentric bores which hold bearing 36. The interior of jacket 38 is a fluid chamber filled with a coolant such as water. The coolant is circulated by means of inlet 42 and outlet 44 around bearing 36. The breadth of tank 40 is about the same as and, in this embodiment slightly exceeds, the breadth of the upper test chambers, described further hereinafter. The volume of tank 40 can be designed in dependence upon the expected heat generation, rate of fluid flow, volume available, etc.

The upper end of shaft 34 comprises a threaded stud, on which is mounted test specimen 47. This specimen is a disc of the material whose erosion characteristics is to be measured. While disc 47 may be almost any size, it is expected that its diameter will vary between one to twelve inches. Most preferably disc 47 is ⅜ inch thick and has a diameter of 3 inches. The size chosen will depend upon the conditions being simulated. For example, if the angular speed of motor 14 is insufficiently high, then it may be desirable to increase the diameter of specimen 47 to increase its tangential velocity.

An enclosure is shown herein as steel drum 46 having cylindrical walls and domed lid 48. Enclosure 46 can be secured to jacket 38 by placing it around jacket 38 on the inside of annular guide band 50 and resting atop the upper portion of legs 12. Enclosure 46 has appropriate notches cut into its bottom edge to avoid interference with circulation pipes 42 and 44. If it is desirable to have a very tight or even a gas tight seal, appropriate sealing devices can be employed between enclosure 46 and jacket 38.

Enclosure 46 has a thermally insulating lining consisting of annular liner 54 and circular cap liner 56 adjacent to domed lid 48. Also shown is a lower liner 58 resting atop jacket 38. Liners 54, 56, and 58 are preferably a conventional insulation such as ceramic fiber, but any other suitable insulating material can be used. It will be appreciated that this insulating layer may be used to limit temperature changes and the passage of heat through enclosure 46.

Enclosure 46 can be filled, either partially or completely, through upper inlet 60, piercing domed top 48 and upper liner 56. Also, enclosure 46 can be emptied through a lower outlet 61, piercing the side of enclosure 46 and insulating liner 54. Enclosure 46 is shown partially filled with abrasive medium 62, shown herein as a multiplicity of particles. The particles chosen depend upon the abrasives present under service conditions. For example, the particles can be coal, catalyst, sand, shale, silicon carbide and/or other materials. The size of these particles will be chosen to simulate the service conditions. Medium 62 can be a granulate, particulate, or powder having sizes preferably in a range of 10 to 1000 $\mu$m, although other sizes can be used if necessary to simulate the service environment. Also, abrasive medium 62 may be disposed in a gaseous medium that simulates the gaseous ambient in the service environment. To this end, it may be desirable to make enclosure 46 gas tight to contain such a gaseous ambient.

Figure 2:
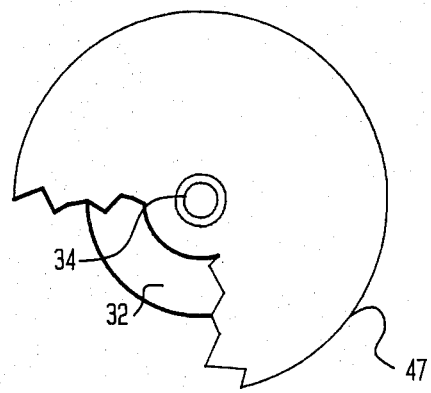
FIG. 2 is a plan view of the specimen of FIG. 1 with a portion broken away to reveal the underlying bearing elements.
Figure 3:
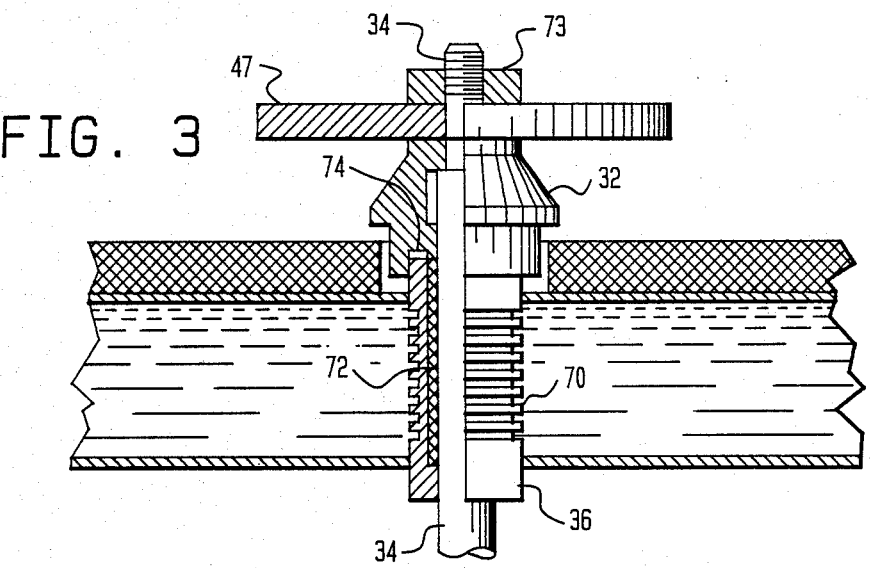
FIG. 3 is a detailed view of the bearing and specimen of FIG. 1, partially sectioned to reveal interior components of the bearing.

Referring to FIGS. 2 and 3, a detailed plan and elevational view, respectively, is given of the spindle means of FIG. 1. Previously illustrated shaft 34 is shown to be a shaft having a reduced-diameter, upper threaded stud. The bearing is shown herein comprising a generally cylindrical casing 36 having a plurality of spaced, annular, cooling ribs 70. Casing 36 contains a high temperature, carbon bearing 72 which is non-rotating and which supports and allows rotation of shaft 34. Hub 32 is shown as a generally cylindrical, bored body having an upper, frustro-conical cap whose upper peak is formed into a short cylindrical stub on which specimen 47 rests. It will be appreciated that nut 73 or similar device will be threaded onto the upper stud of shaft 34 to secure specimen 47 onto hub 32 so that specimen 47, shaft 34 and hub 32 rotate together. A seal 74 is pressed against an interior shoulder of hub 32 by the upper end of housing 36. This seal prevents particles of the abrasive medium from reaching and damaging bearing 72.

Figure 4:
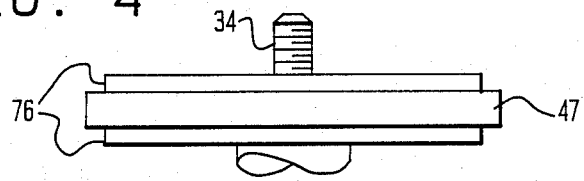
FIG. 4 is a detailed side view of an alternate mounting arrangement for the specimen of FIG. 1.

An alternate mounting for specimen 47 is shown in FIG. 4 wherein a pair of complementary discs 76 sandwich specimen 47 and limit erosion to primarily the periphery of the specimen.

Figure 5:
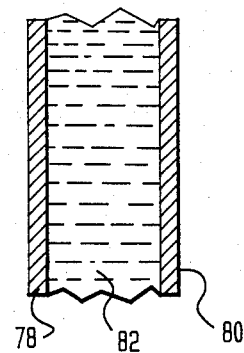
FIG. 5 is a detailed cross-sectional veiw of an alternate wall construction for the enclosure of FIG. 1.

Referring to FIG. 5 an alternate construction is shown for the enclosure (enclosure 46 of FIG. 1). In this embodiment, the side of enclosure 46 comprises duplex walls 78 and 80 encompassing a circulating fluid such as water. The temperature of circulating fluid 82 can be maintained to either heat or cool the contents of the enclosure. Alternatively the fluid prevents damage to the enclosure which may occur due to excessively hot abrasive mediums.

To facilitate an understanding of the principles associated with the foregoing test apparatus, its operation will now be briefly described. Assume initially that enclosure 46 and specimen 47 have been removed. Since the service environment to be simulated involves particles of a predetermined size, composition and temperature in a specific gaseous environment, such an abrasive medium is obtained. The abrasive medium is then heated (or cooled) at a location apart from the test apparatus. Next, specimen 47 made from a known weight of the material whose erosion properties are to be tested is secured to the upper stud of shaft 34 by a nut. Thereafter enclosure 46 is installed over and sealed to jacket 38. Abrasive medium 62 at the appropriate temperature is next supplied through inlet 60 to either partially or completely fill enclosure 46. At this time also, circulation may be induced through conduits 42 and 44 to insure that excessive heat does not build up in bearing 36.

At this time, rheostat 18 may be set to adjust the angular speed of motor 14. Motor 14 is set to produce a tangential velocity on specimen 47 corresponding to particle velocity in the service environment. Note that the peripheral tangential velocity selected may be somewhat greater than the average particle velocity to account for the fact that the velocity is less toward the center of specimen 47. The speed of motor 14 may be measured directly by a tachometer or by other means. In the embodiment, angular speed is measured by noting the number of revolutions accumulated on counter 28 over a time interval measured by the stop watch 30, the ratio obviously being velocity. Once velocity is thus measured and adjusted, the specimen may be spun for a predetermined number of revolutions or a predetermined time (for example, 5 minutes) which interval will be chosen based upon the susceptibility of the specimen to wear.

Thereafter, motor 14 is stopped and abrasive medium 62 is removed through outlet 61. Thereafter, enclosure 46 can be lifted and removed before removing specimen 47 from the stud of shaft 34. Next, specimen 47 is cleaned in an ultrasonic bath and weighed to determine its weight loss. Thereafter, the test apparatus can be reassembled by reinstalling specimen 47 on stud 34, replacing enclosure 46 and refilling it through inlet 60 with fresh or with reheated abrasive medium. Motor 14 is restarted to run at the previously set angular speed and for the same duration. (Of course alternate durations can be chosen if the wear appears too small or great).

It will be appreciated that the foregoing steps can be repeated so that the successive weight reduction of specimen 47 can be plotted as a function of the total elapsed time (or revolutions) over which the specimen is subjected to spinning and wearing. It has been found that the wear quickly converges to a constant linear rate. This linear plot is an accurate representation of the wear rate. Once the wear rate has been determined under these simulated conditions, closely matching service conditions, one can accurately estimate the annular wear rate under actual service conditions.

An alternate test method can be employed. Instead of removing specimen 47 and measuring its weight reduction, the reduction in its diameter can be measured. This test technique has the virtue that the particle velocity is consistent since particles impinging the outer periphery of the specimen 47 experience the same tangential velocity. Accordingly, the spinning of specimen 47 can be interrupted, the abrasive medium 62 removed through outlet 61, and the enclosure 46 removed to allow measurement of the outside diameter of the specimen. By repeating this sequence, the resulting measurements can again be plotted until a linear relation with time is obtained so that annual wear rate can be estimated.

If the shielding discs 76 (FIG. 4) are employed, the wear of specimen 46 occurs only at the outer periphery. Thus the wear can be localized and very accurately measured. However, the discs are not necessary when the test is performed by measuring diametric changes.

It is to be appreciated that various modifications may be implemented with respect to the above described preferred embodiment. For example, while a cylindrical enclosure is disclosed, rectangular or other shapes may be used instead. Furthermore, while a specimen having even thickness is described, this thickness can be graded depending upon the application. Also while direct drive of the specimen by a motor is disclosed, intermediating drives, transmissions or reducers can be used as well. It is also expected that the various components disclosed herein can be fabricated from steel, aluminum, other metals, plastics, ceramics or other materials depending upon the desired strength, heat resistance, reliability, rigidity, insulating properties, vibration immunity, etc. Moreover, while the enclosure may be opened by removing it from the underlying water jacket, in other embodiments the enclosure may have a removable top, side panel or access plate. Furthermore, while the water jacket disclosed herein comprises the bottom of the enclosure, it is anticipated that in some embodiments the enclosure may have its own integral bottom independent of the water jacket. In addition, various types of bearings may be employed to support and allow spinning of the specimen, including ball bearings and other types of bearings.

Obviously many modifications and variations of the present invention are possible in light of the above teachings. It is therefore to be understood that within the scope of the appended claims, the invention may be practiced otherwise than as specifically described.

What is claimed is:

1. Test apparatus for testing the erosion resistance of a specimen comprising:
   an enclosure encompassing a test chamber;
   an abrasive medium disposed in said enclosure;
   spindle means attached to said enclosure, said spindle means having an inside end adapted to hold said specimen, said spindle means including: a shaft and thermal means for moderating temperature within said spindle means and sized to dissipate sufficiently the heat originating from said enclosure away from said spindle means to avoid distortions thereof, said thermal means including a heat exchanging jacket having a fluid chamber encircling said shaft;
   cover means secured about said spindle means for shielding said specimen except at its periphery from erosion by said abrasive medium; and
   motor means coupled to said spindle means for spinning said inside end at an adjustable angular speed within said medium, so that said specimen can be eroded at its periphery with a uniform particle impingement speed and with no substantial erosion occurring at radially inward locations shielded by said cover means.

2. Test apparatus according to claim 1 wherein said fluid chamber is annular and wherein said shaft is rotatably mounted through said jacket, said cover means further comprising:

a pair of complementary discs, said specimen being sandwiched between said discs, said discs each having an outside diameter about the same as said specimen.

3. Test apparatus according to claim 2 wherein said spindle means further comprises:

a bearing mounted through and encircled by said jacket, said shaft being rotatably mounted in and extending through said bearing.

4. Test apparatus according to claim 1 wherein said enclosure has a closed top and open bottom, said jacket being sized to fit into and close said open bottom of said enclosure.

5. Test apparatus according to claim 1 wherein said fluid chamber has an interior breadth about the same as said enclosure.

6. Test apparatus according to claim 1 wherein said enclosure has a thermally insulating lining.

7. Test apparatus according to claim 1 wherein said angular speed of said motor means is adjustable to exceed 1000 revolutions per minute.

8. Test apparatus according to claim 7 wherein said angular speed of said motor means is adjustable to exceed 10,000 revolutions per minute.

9. Test apparatus according to claim 1 wherein said abrasive medium comprises:

a multiplicity of particles.

10. Test apparatus according to claim 9 wherein said particles are selected from the group consisting of coal, catalyst, sand, shale or silicon carbide.

11. Test apparatus according to claim 9 or 10 wherein said particles fall within a predetermined range of sizes.

12. Test apparatus according to claim 8 further comprising:

a counter coupled to said spindle means to count the number of its revolutions.

13. Test apparatus according to claim 1 wherein said cover means comprises:

a pair of complementary discs, said specimen being sandwiched between said discs, said discs each having an outside diameter about the same as said specimen.

14. Test apparatus according to claim 12 wherein said enclosure comprises:

an upper inlet and lower outlet for adding to and removing from, respectively, said test chamber said medium.

15. Test apparatus according to claim 1 wherein said enclosure includes:

means for inducing a predetermined gaseous ambient within said enclosure.

16. Test apparatus according to claim 15 wherein said abrasive medium comprises:

a multiplicity of particles.

17. Test apparatus according to claim 13 further comprising:

means for measuring the angular speed of said inside end.

18. Test apparatus according to claim 13 wherein said motor means comprises:

means for adjusting the motor speed.

19. Test apparatus for testing the erosion resistance of a specimen comprising:

an enclosure encompassing a test chamber;
an abrasive medium disposed in said enclosure;
spindle means attached to said enclosure, said spindle means having an inside end adapted to hold said specimen;
cover means secured about said spindle means for shielding said specimen except at its periphery from erosion by said abrasive medium;
motor means coupled to said spindle means for spinning said inside end at an adjustable angular speed within said medium, so that said specimen can be eroded at its periphery with a uniform particle impingement speed and with no substantial erosion occurring at radially inward locations shielded by said cover means, said angular speed of said motor means being adjustable to exceed 10,000 revolutions per minute; and
a counter coupled to said spindle means to count the number of its revolutions, said counter including:
a reflective target mounted on said spindle means to rotate synchronously with its inside end; and
an optical transceiving means for sensing the passage of said target.

20. Test apparatus for testing the erosion resistance of a specimen comprising:

an enclosure encompassing a test chamber;
an abrasive medium disposed in said enclosure;
spindle means attached to said enclosure, said spindle means having an inside end adapted to hold said specimen, said spindle means having cover means secured about said spindle means for shielding said specimen except at its periphery from erosion by said abrasive medium, said cover means including at least one disc overlaying said specimen; and
motor means coupled to said spindle means for spinning said inside end at an adjustable angular speed within said medium, so that said specimen can be eroded at its periphery with a uniform particle impingement speed and with no substantial erosion occurring at radially inward locations shielded by said cover means.

21. Test apparatus for testing the erosion resistance of a speciment comprising:

an enclosure encompassing a test chamber, said enclosure being double-walled;
an abrasive medium disposed in said enclosure;
spindle means attached to said enclosure, said spindle means having an inside end adapted to hold said specimen, said enclosure containing fluid circulating at said spindle means to dissipate sufficiently the heat originating from said enclosure away from said spindle means to avoid distortions thereof;
cover means secured about said spindle means for shielding said specimen except at its periphery from erosion by said abrasive medium; and
motor means coupled to said spindle means for spinning said inside end at an adjustable angular speed within said medium, so that said specimen can be eroded at its periphery with a uniform particle impingement speed and with no substantial erosion occurring at radially inward locations shielded by said cover means.

22. A method for testing the erosion properties of a specimen exposed to glancing impingement by particles having a given speed, comprising the steps of:

embedding said specimen in a multiplicity of said particles;
shielding said specimen except at its periphery from abrasion by said particles;

spinning said specimen at an angular velocity bearing a given relation to said given speed; and measuring the extent of erosion from said specimen; and remeasuring the extent of said erosion periodically, whereby said specimen can be eroded at its periphery with a uniform particle impingement speed and with no substantial erosion occurring at radially inward, shielded locations.

23. A method according to claim 22 further comprising the step of:

heating said particles to a predetermined temperature.

24. A method according to claim 22 further comprising the steps of:

removing and cleaning said specimen from said particles; and measuring the reduction in weight of said specimen.

25. A method according to claim 22 further comprising the step of:

measuring the change in diameter of said specimen.

26. A method according to claim 25 further comprising the step of:

covering the top and bottom of said specimen to limit erosion.

27. A method according to claim 22 comprising the step of:

measuring the number of revolutions of said specimen.

28. A method according to claim 22 or 27 comprising the step of:

measuring the angular speed of said specimen.

29. A method according to claim 28 comprising the step of:

measuring the temperature of said multiplicity of said particles.

30. A method according to claim 22 wherein said remeasuring is repeated at least until the rate of erosion stabilizes.

31. A method according to claim 22 wherein said rate of erosion is scaled to an annual amount of erosion by multiplying said rate by a predetermined factor.

32. A method according to claim 22 employing a spindle and comprising the steps of:

mounting said specimen on said spindle and spinning both; and applying coolant to said spindle as it spins.

33. A method according to claim 22 comprising the step of:

inducing a given gaseous ambient upon said specimen as it spins.

34. A method according to claim 22 comprising the step of:

cooling said particles.

35. A method according to claim 22 comprising the step of:

altering from ambient the temperature of said particles before embedding said specimen therein.

* * * * *